(12) United States Patent
Ellison et al.

(10) Patent No.: US 7,511,732 B2
(45) Date of Patent: Mar. 31, 2009

(54) ASSEMBLY AND METHOD FOR SECURING AN ENDOSCOPE TO A DIGITAL CAMERA

(75) Inventors: Lars Magnus Ellison, Sacramento, CA (US); Nicholas John Hellenthal, Sacramento, CA (US); Edward L. Herrmann, Grass Valley, CA (US)

(73) Assignee: Crucible Technologies, LLC, Sacramento, CA (US)

( * ) Notice: Subject to any disclaimer, the term of this patent is extended or adjusted under 35 U.S.C. 154(b) by 310 days.

(21) Appl. No.: 11/534,213

(22) Filed: Sep. 21, 2006

(65) Prior Publication Data

US 2007/0229655 A1  Oct. 4, 2007

Related U.S. Application Data

(60) Provisional application No. 60/743,966, filed on Mar. 30, 2006.

(51) Int. Cl.
*A62B 1/04* (2006.01)
*H04N 7/18* (2006.01)
*H04N 9/47* (2006.01)

(52) U.S. Cl. ...................................................... 348/65
(58) Field of Classification Search ......... 248/674–678; 361/600; 403/113
See application file for complete search history.

(56) References Cited

U.S. PATENT DOCUMENTS 5,850,789 A * 12/1998 Rudolf et al. ............... 101/486
6,155,973 A   12/2000 Howes et al.
6,382,494 B1 * 5/2002 Miller ......................... 228/1.1
6,594,516 B1   7/2003 Steckner et al.
2003/0038223 A1 * 2/2003 Fleming et al. ............. 248/564
2004/0135885 A1   7/2004 Hage
2005/0203415 A1 * 9/2005 Garlick et al. .............. 600/463
2005/0207744 A1 * 9/2005 Yano ........................... 396/55
2005/0270379 A1   12/2005 Seo
2006/0050173 A1 * 3/2006 Ajioka ........................ 348/373

OTHER PUBLICATIONS

International Search Report dated Jul. 28, 2008, received in corresponding International Patent Appl. No. PCT/US2007/065720.
Melder et al., "Endoscopic Photography," Arch Otolaryngology Head & Neck Surgery, May 2003, vol. 129; pp. 570-575.

(Continued)

*Primary Examiner*—Nhon T Diep

(57) ABSTRACT

An assembly for securing the eyepiece of an endoscope to a digital camera includes a bar that supports the camera and a block that supports the eyepiece. The camera can be secured to the bar using the camera's tripod mounting hole. The block can normally move in three orthogonal linear directions relative to the bar, but can also be locked in a selected position relative to the bar. In this manner, the assembly can be adjusted so that the eyepiece of the endoscope contacts or nearly contacts the end of the barrel of the digital camera secured to the camera bar. Then, the support block can be locked into position to clamp the endoscope to the digital camera. A sheet is attached to one of the components and can be draped over the camera prior to use of the camera in a sterile environment.

19 Claims, 8 Drawing Sheets

OTHER PUBLICATIONS

PubMed abstract of Kakizaki et al., "Photography of the endoscopic picture with a consumer-grade digital camera," Nippon Hinyokika Gakki Zasshi, Sep. 2003, vol. 94, No. 6; pp. 639-642.

Tsunoda et al., "High Quality Video Recording and Monitoring Systems for Endoscopes," The Laryngoscope, Aug. 2005, vol. 115; pp. 1115-1121.

Truzzi et al., "A Simple Way to Take Pictures During Endscopic Procedures," The Journal of Urology, Jan. 2004, vol. 171; pp. 327-338.

Tsunoda et al., "Endoscopic Adaptor for Digital Camera and Digital Image Filing," The Laryngoscope, Jul. 2002, vol. 112; pp. 1308-1309.

* cited by examiner ic
ASSEMBLY AND METHOD FOR SECURING AN ENDOSCOPE TO A DIGITAL CAMERA This application claims the benefit of U.S. Provisional Application No. 60/743,966, filed Mar. 30, 2006, the entire disclosure of which is hereby incorporated by reference.

BACKGROUND OF THE INVENTION

1. Field of the Invention

The present invention relates generally to endoscopy. In particular, the present invention relates to an assembly for securing any readily-available digital camera to the eyepiece of an endoscope.

2. Description of Current Technology

Endoscopy is a visual diagnostic tool that is applied in many fields of medicine. In endoscopy, a long narrow flexible tube, i.e., an endoscope, is used to transmit an image of an object located near a first one of its ends to a second one of its ends. The first end is inserted into a body. The interior of the endoscope is capable of transmitting light entering the first end of the endoscope to the second end of the endoscope. The second end of the endoscope usually has an eyepiece so that a person can view the transmitted image of the object located near the first end of the endoscope.

Because of its narrow tubular structure, the endoscope is a useful tool for viewing the inside of a body lumen. For example, in a procedure called cystoscopy, a urologist uses an endoscope to visually inspect the urethra and urinary bladder for abnormalities. Endoscopic procedures outside the field of urology include but are not limited to colonoscopy (gastroenterology), bronchoscopy (otolaryngology), and tympanoscopy (pediatrics).

While it is possible to view an image of an object located near the first end of the endoscope by physically looking through the eyepiece at the second end of the endoscope, this method of viewing the image is limiting in the sense that only one person can view the image at a time and that person will often have to be in a particular location in a room in order to view the image. It is more useful to display the image on a monitor so that any person in the room can view it without moving to a particular location in the room. This is particularly useful during a surgical procedure, where a surgeon often needs to be at a particular location and cannot move from that location for purposes of viewing the image.

Additionally, often a doctor will want a physical record of an image from an endoscope. Such a physical record, i.e., a photograph, can, for example, be placed in a patient's paper file.

Currently, a large tower containing an analog camera linked to a monitor is used to display an image from an endoscope and to capture the image for a permanent record. This equipment is large, difficult to use, non-portable, and expensive. The cost of this equipment can be $40,000 or more and the non-portability of the equipment means that endoscopic procedures must be performed in a dedicated room. Additionally, because the camera is analog, i.e., the image is captured on film, the image cannot easily be incorporated into an electronic patient file.

Compact digital cameras are inexpensive, portable and readily available. A digital camera can be purchased for $500 or less. Digital cameras can capture images that can be easily downloaded into a computer, which can readily incorporate them into electronic patient files. Most digital cameras can also record video. Digital cameras also contain a port for plugging in a cable from a TV or a monitor for live display of the images received by the barrel of the camera. Newer digital cameras are able to wirelessly transmit images to a computer for storage or to a compatible monitor or TV for display. Some cameras can even wirelessly transmit a video being taken by the camera to a monitor or TV in real-time. Due to their popularity, new features are continuously being added to digital cameras and their prices continue to fall.

Attempts have been made in the past to use a digital camera in endoscopic procedures, with varying success. For a digital camera to be employed in endoscopy, it must be positioned against the eyepiece at the second end of the endoscope. Digital cameras, however, differ considerably in their size and construction. The barrels of some digital cameras are located at the center of the front face of the camera. The barrels of other digital cameras are located on a particular side of the front face. Additionally, the size of the barrel and the amount by which the barrel extends from the front face differs from camera to camera. Therefore, it is difficult to construct a universal mechanism that secures any common digital camera to the eyepiece of the endoscope.

SUMMARY OF THE INVENTION

It is an object of the invention to construct an assembly that secures any readily-available digital camera to the eyepiece of an endoscope.

It is a further object of the invention to construct the assembly so that it accounts for the variations between different digital-camera models.

It is a still further object of the invention to maintain a sterile condition within a room when using an off-the-shelf digital camera during an endoscopic procedure.

These objects and others are accomplished by an assembly according to the present invention. Such an assembly comprises a camera bar. The camera bar is adapted to be connected to the bottom of a digital camera. A second bar is slidably connected to the camera bar such that the camera bar and the second bar can move relative to each other along a first axis. A bracket is slidably connected to the second bar such that the bracket and the second bar can move relative to each other along a second axis that is orthogonal to the first axis. A block is slidably connected to the bracket such that the block and the bracket can move relative to each other along a third axis that is orthogonal to both the first axis and the second axis. The block includes a cavity that is adapted to receive the barrel of a digital camera and an eyepiece of an endoscope.

BRIEF DESCRIPTION OF THE DRAWINGS

Additional aspects, features, and advantages of the invention, both as to its structure and operation, will be understood and will become more readily apparent when the invention is considered in light of the following description made in conjunction with the accompanying drawings, wherein.

DETAILED DESCRIPTION OF PREFERRED EMBODIMENTS

Figure 1:
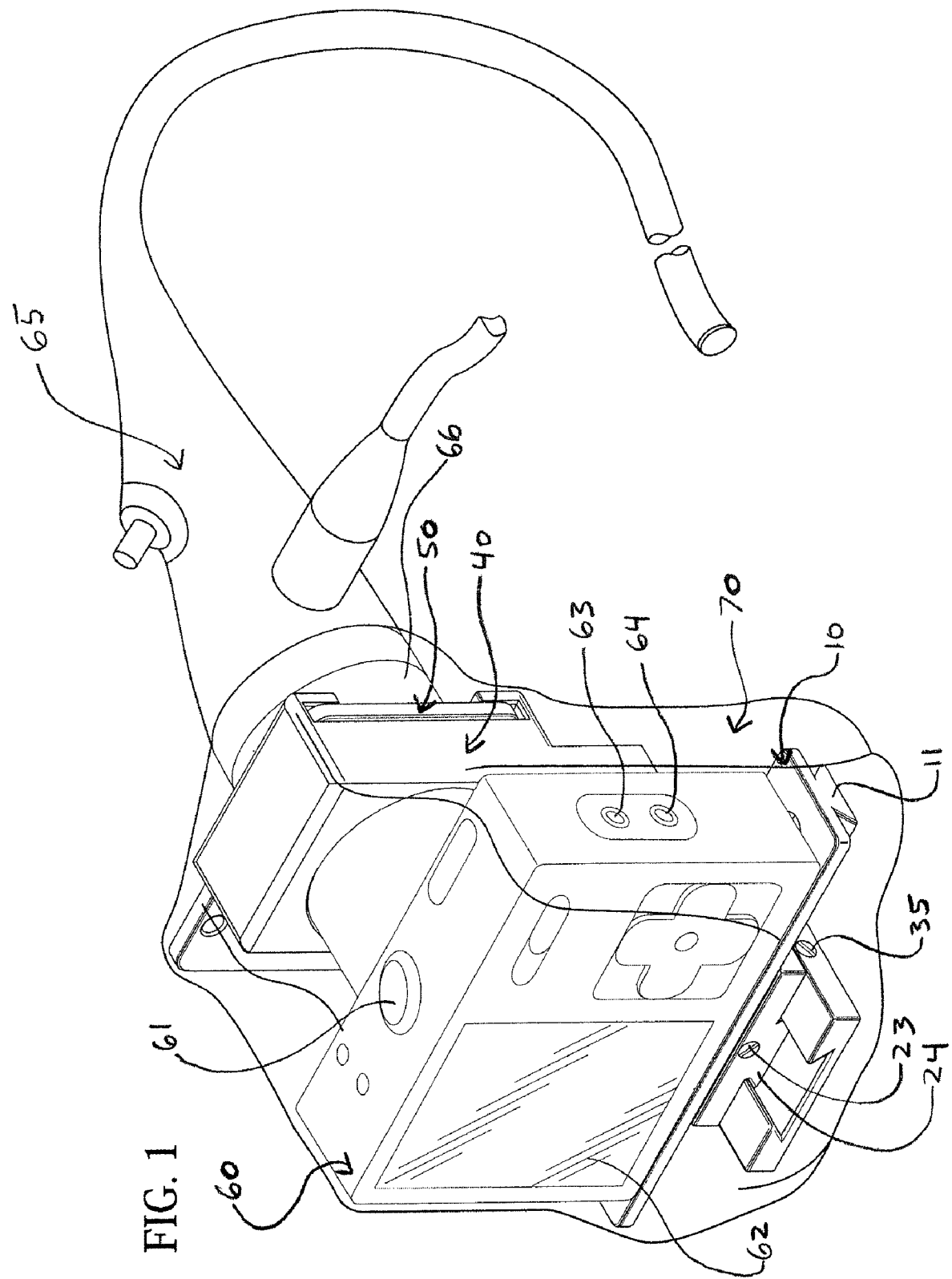
FIG. 1 is a perspective view of an assembly that embodies the invention along with a digital camera and an endoscope.
Figure 2:
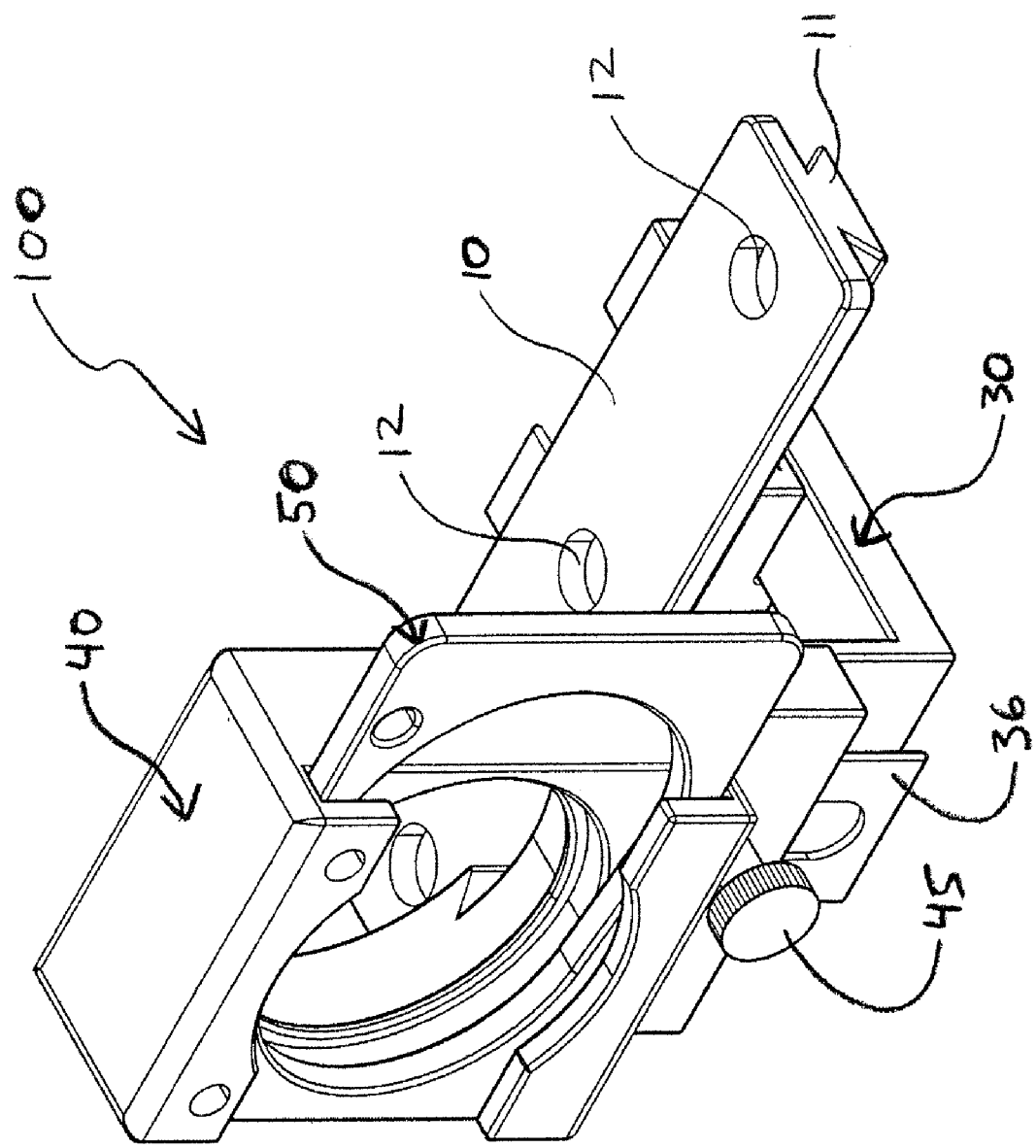
FIG. 2 is a perspective view of the assembly shown in FIG. 1.
Figure 3:
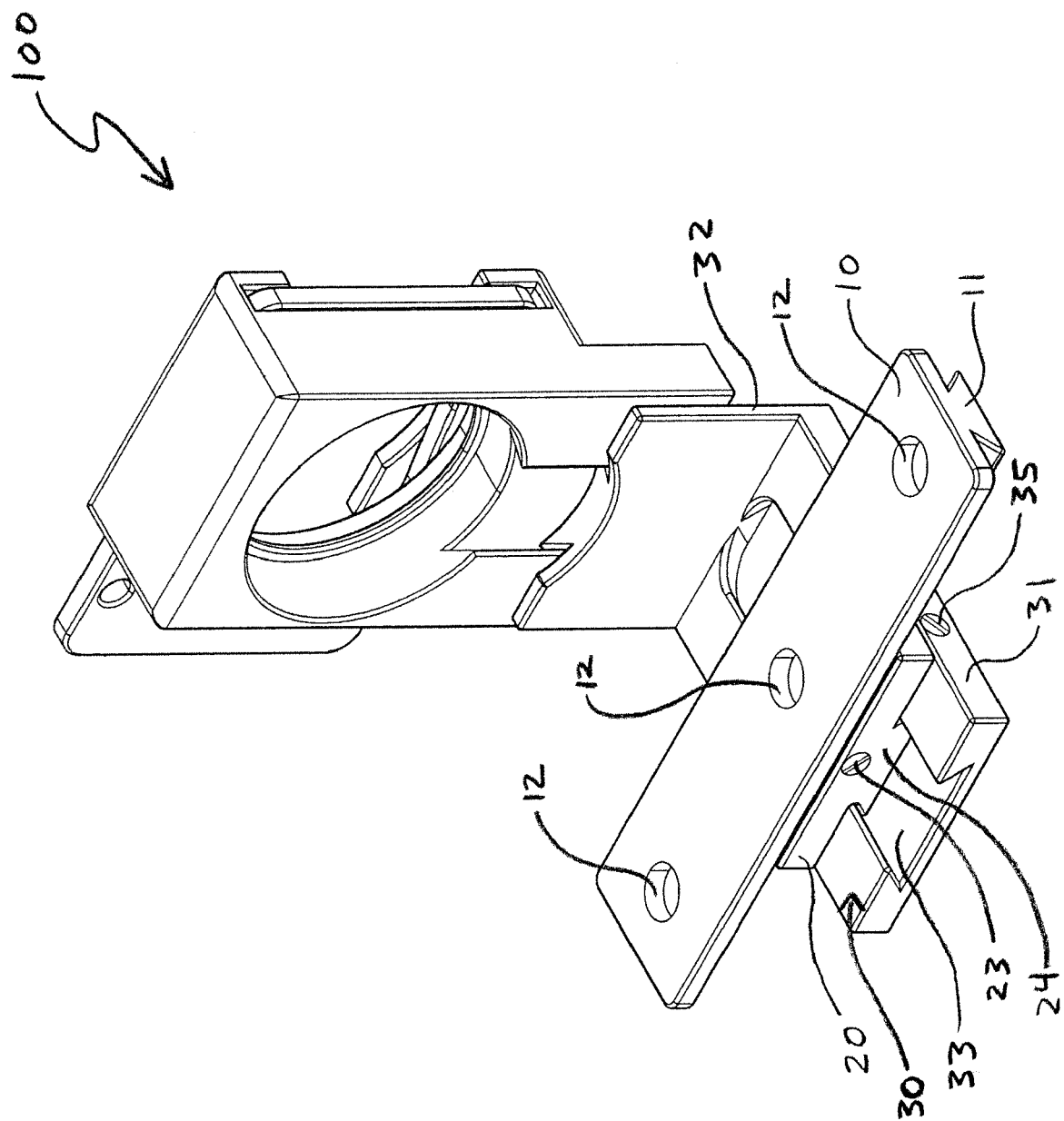
FIG. 3 is another perspective view of the assembly shown in FIG. 1 from a different viewing angle.

The preferred embodiments of the present invention will be described below and with reference to the accompanying drawings. The present invention(s) may, however, be embodied in many different forms and should not be construed as limited to the embodiments described herein or shown in the drawings.

The present application is directed to an assembly for securing an endoscope to any off-the-shelf digital camera. The assembly includes a first component that supports the digital camera and a second component that supports the eyepiece of the endoscope. The second component can be moved in three orthogonal linear dimensions relative to the first component so that the eyepiece can be put in contact or near contact with the end of the barrel of the camera. Once the second component is properly positioned, it can be locked so that it can no longer move relative to the first component. Once properly positioned, the second component serves as an interface that facilitates transfer of images at the eyepiece of the endoscope to the digital camera. The assembly allows for a universal connection between an endoscope eyepiece and any digital camera. A sheet can be draped over the assembly and the camera so that the assembly and camera do not affect the sterility of the room or the operation or examination instruments. The connection between the first component and the camera can take advantage of the fact that practically all digital cameras contain a threaded hole on their bottom surface for mounting to a tripod.

FIGS. 1-9 show the elements of an assembly 100 according to an embodiment of the invention. A camera bar 10 has a length that is longer than that of most digital cameras and is generally flat in shape. A male dovetail 11 extends along the full length of the camera bar at its bottom surface. The camera bar includes three holes 12 along its length. The holes extend from the top surface of the camera bar to the bottom surface. Each one of the holes is large enough such that the threaded portion of a screw 90 (FIG. 4) that can mate with the tripod mounting hole in an off-the-shelf digital camera can pass through the hole. Practically all models of digital cameras contain a screw hole for mounting the camera to a standard camera tripod. The holes in the camera bar may also have internal threads of the same type as the tripod mounting hole. The camera bar includes three holes to account for the fact that the location of the tripod mounting hole differs from camera model to camera model. In some camera models, the tripod mounting hole is located at the center of the bottom surface of the camera, and in other camera models it is offset to one side of the bottom surface of the camera.

The digital camera 60, which is shown in FIG. 1, will generally include a shutter button 61 for capturing an image. The digital camera may include an LCD screen 62 on its back side for viewing the images received by the camera or the images captured by the camera by using the shutter button. The digital camera may further include a port 63 for receiving a cable that can be connected at its opposite end to a computer for downloading pictures to the computer and a port 64 for receiving a cable that can be connected at its opposite end to a television or computer monitor for viewing still images or live video from the camera on a TV or monitor. Alternatively, the camera may be wirelessly enabled, such that it can wirelessly download images to a computer and can wirelessly transmit images or video to a wireless-enabled monitor or TV. Because the digital camera is mounted to the assembly on its bottom side, the assembly does not interfere with any of the functionality of the camera. An operator can access all of the buttons on the camera to, for example, adjust the focus, zoom in and out, capture a still image, or record a video with or without audio overlay.

Figure 4:
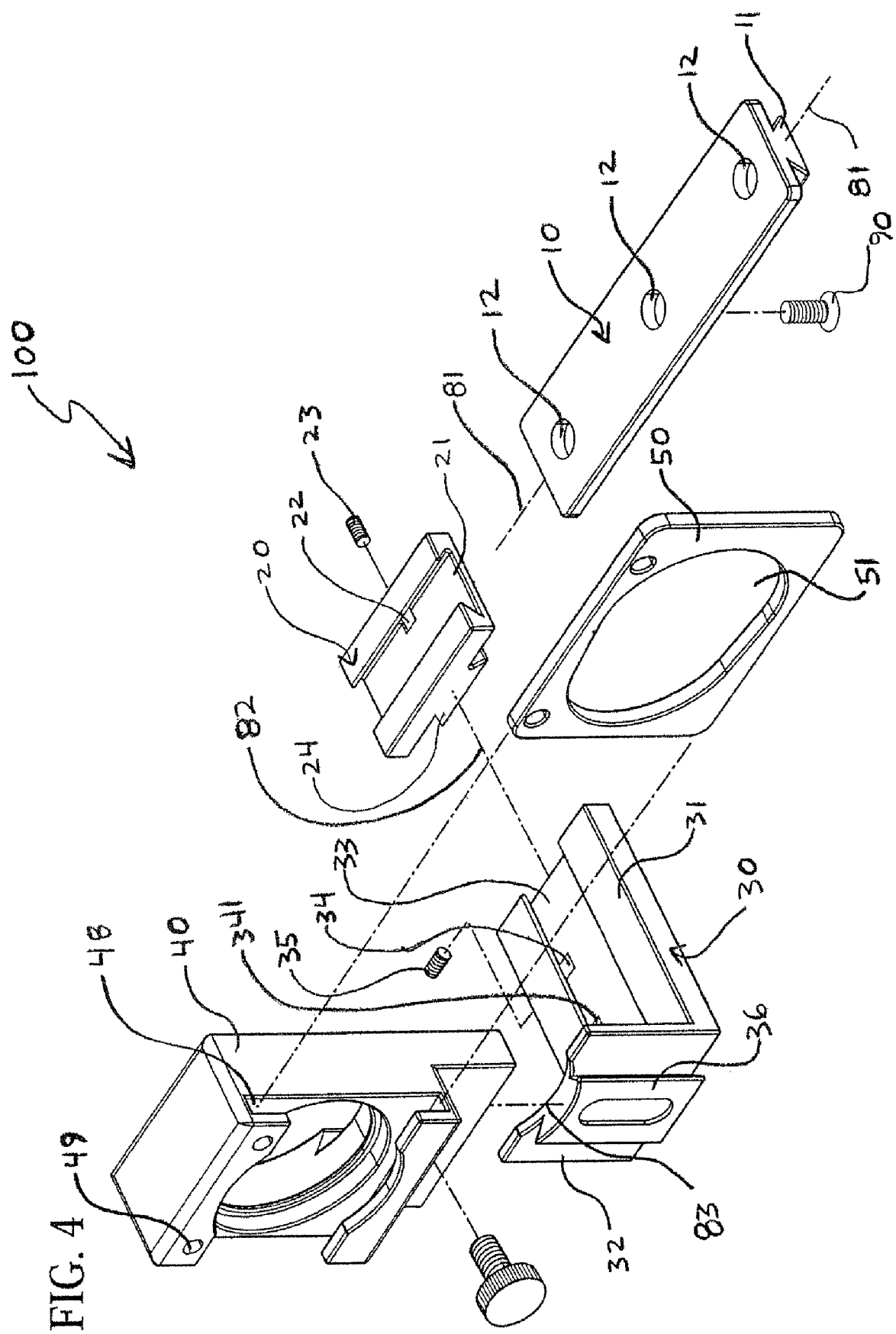
FIG. 4 is an exploded view of the assembly shown in FIG. 1.

A second bar 20 includes a female dovetail 21 on its top surface. The female dovetail 21 slides on the male dovetail 11 on the camera bar 10. This allows the second bar 20 to move relative to the camera bar 10 along a first axis 81 (FIG. 4). One side of the second bar 20 has a threaded hole 22 that receives a first set screw 23. The first set screw 23 can lock the second bar 20 in a particular position relative to the camera bar 10. The bottom portion of second bar 20 includes a male dovetail 24 that is orthogonal to the female dovetail 21 in the top portion of the second bar.

A bracket 30 that is generally L-shaped includes a horizontal section 31 and a vertical section 32. The top surface of the horizontal section includes a female dovetail 33. The female dovetail 33 slides along the male dovetail 24 on the second bar 20. This allows the bracket 30 to move relative to the second bar 20 along a second axis 82 (FIG. 4). One side surface of the horizontal section 31 includes a threaded hole 34 that receives a second set screw 35. Similar to the first set screw 23, the second set screw 35 can lock the bracket 30 in a particular position relative to the second bar 20. The same side surface of the horizontal section 31 may contain an additional threaded hole 341 and another set screw (not shown) located at a different position along the length of the horizontal section 31 to extend the range of moveability of the bracket 30 with respect to the second bar 20. The vertical section 32 of the bracket 30 includes a male dovetail 36 on the face of the vertical section that faces away from the horizontal section 31.

A block 40 includes a vertically extending female dovetail 41 on its back face 42. The female dovetail 41 can slide on the male dovetail 36 in the vertical section 32 of the bracket 30. This allows the block 40 to move relative to the bracket 30 along a third axis 83 (FIG. 4). Axes 81, 82 and 83 are all orthogonal to each other. (Although axis 81 would never contact either of the other two axes 82,83 if all three axes were extended indefinitely (axis 81 is above axis 82), axis 81 is still considered as being "orthogonal" to axes 82,83 as that term is used herein, including the claims.) A threaded hole 43 extends from the front face 44 of the block 40 to the back face 42 of the block. The hole receives a third set screw 45. Similar to the first set screw 23 and the second set screw 35, the third set screw 45 is effective to lock the block 40 in a particular position relative to the bracket 30. The third set screw 45 can be larger than the other two set screws as shown because the third set screw supports the weight of at least the block 40. At the location of the threaded hole 43, the front face 44 of the block 40 is recessed.

The block includes a cylindrical cavity 46 extending from its front face 44 to its back face 42. The cavity 46 enables the barrel of the digital camera to interface with the eyepiece of the endoscope. The radius of the cavity 46 is very similar to, but slightly larger than, the radius of the eyepiece. The cavity may include a circular flange 47 that extends inwards—such that its radius is smaller than that of the rest of the cavity 46—at a location that is approximately midway between the front face and the rear face of the block 40. The flange 47 prevents the eyepiece of the scope from extending too far into the cavity 46.

Behind the front face 44 of the block 40, a slot 48 that is generally parallel with the front and back faces of the block 40 extends from one side surface of the block to the opposite side surface of the block. An eyepiece-locking plate 50 can slide within the slot 48. The eyepiece-locking plate 50 is shown by itself in FIG. 8. The eyepiece-locking plate 50 includes a central opening 51. The central opening 51 has a first side section 52, a second side section 53 and a transition section 54. The first side section 52 of the opening 51 is a semicircle having a first radius. The second side section 53 of the opening is a semicircle having a second radius that is smaller than the first radius. The radius of the first side section is larger than the radius of an endoscope eyepiece. The radius of the second side section is approximately equal to the radius of an endoscope eyepiece. The transition section 54 is between the first section 52 and the second section 53. The eyepiece-locking plate 50 also includes a hole 55 at the top of the plate on the same side of locking plate 50 as the second side section 53 of the opening. When the eyepiece-locking plate is in a particular position with respect to the block 40, the hole 55 lines up with a threaded hole in the support block. A screw (not shown) can then be passed through the hole 55 and screwed into the hole in the block 40 to lock the eyepiece-locking plate 50 in position relative to the block 40.

Figure 5:
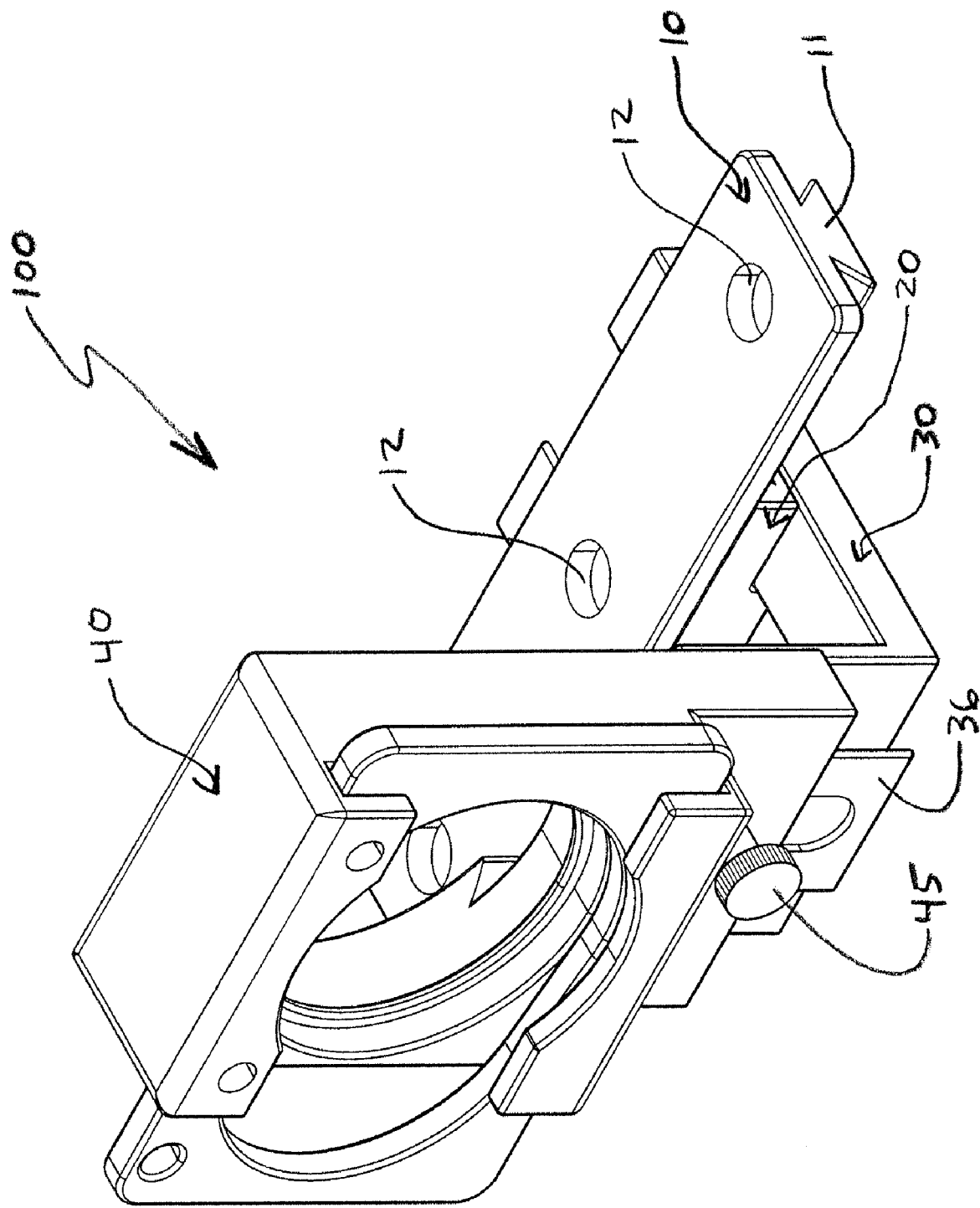
FIG. 5 shows the same perspective view shown in FIG. 2 but with the locking plate of the assembly in a different position.
Figure 6:
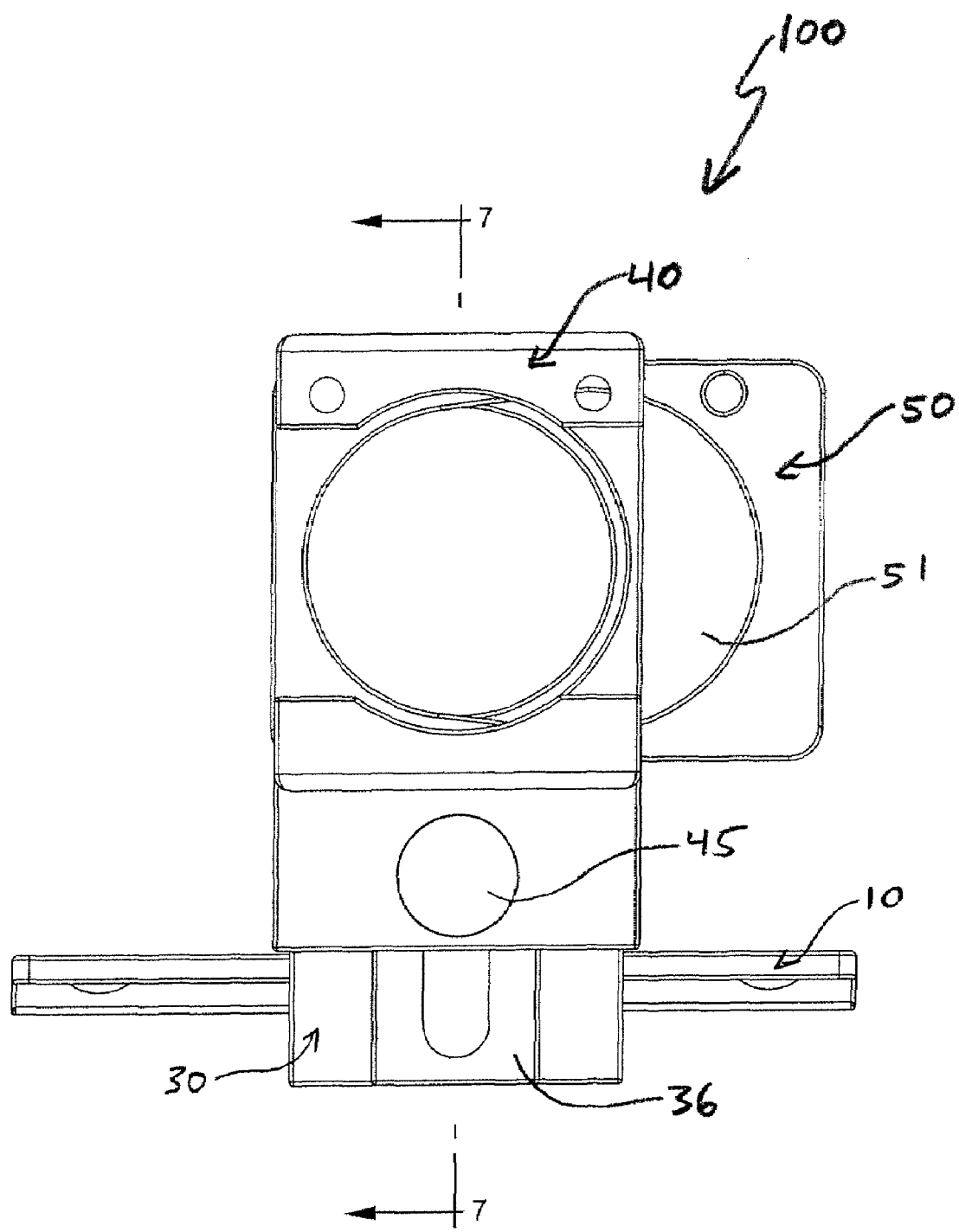
FIG. 6 is a front view of the assembly shown in FIG. 1.
Figure 7:
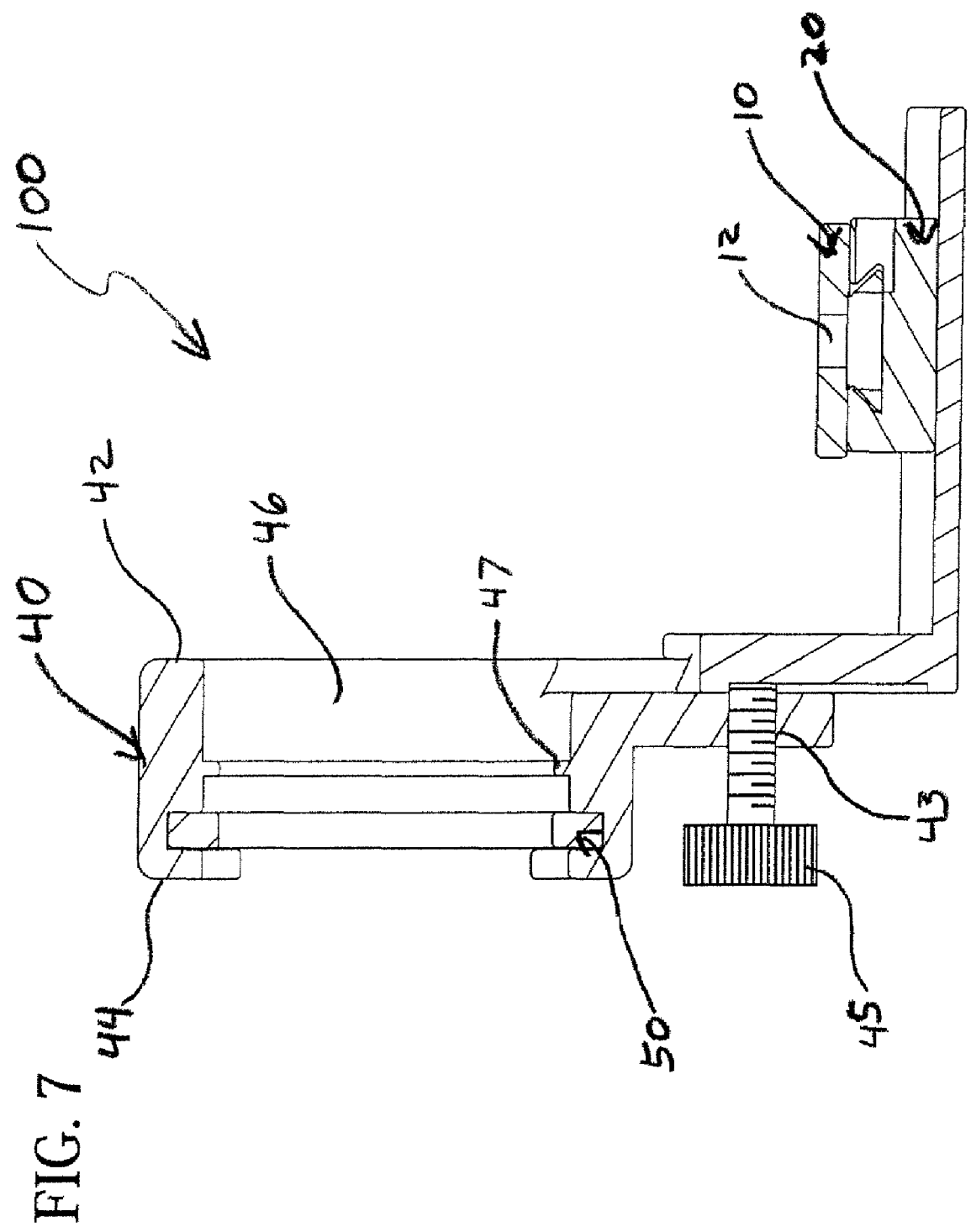
FIG. 7 is a sectional view taken at the cutting plane 7-7 in FIG. 6.
Figure 8:
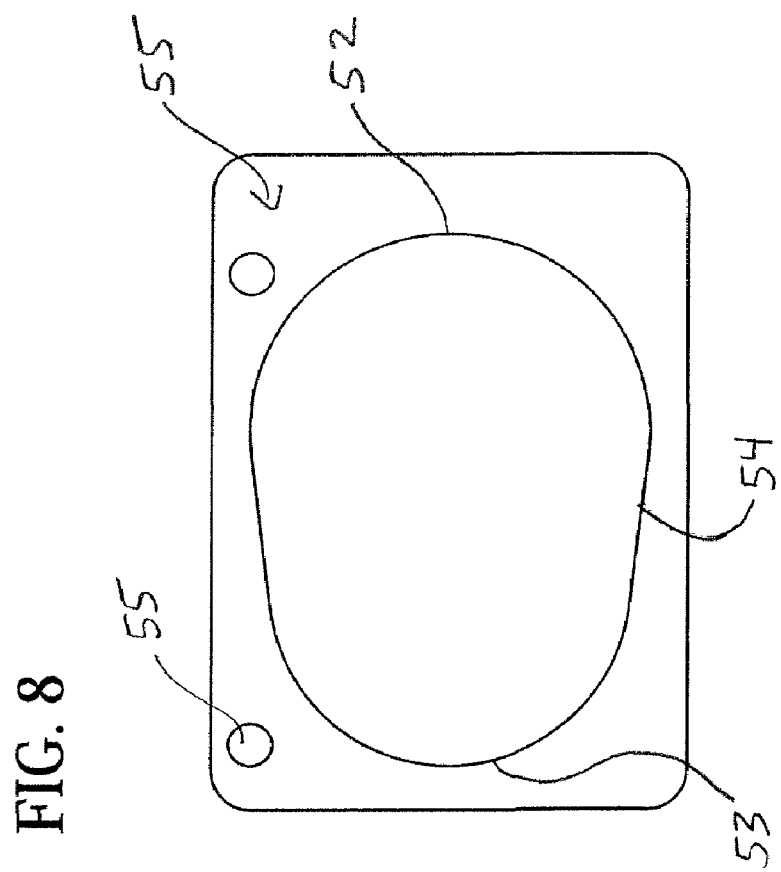
FIG. 8 shows the locking plate that is used in the assembly shown in FIG. 1.
Figure 9:
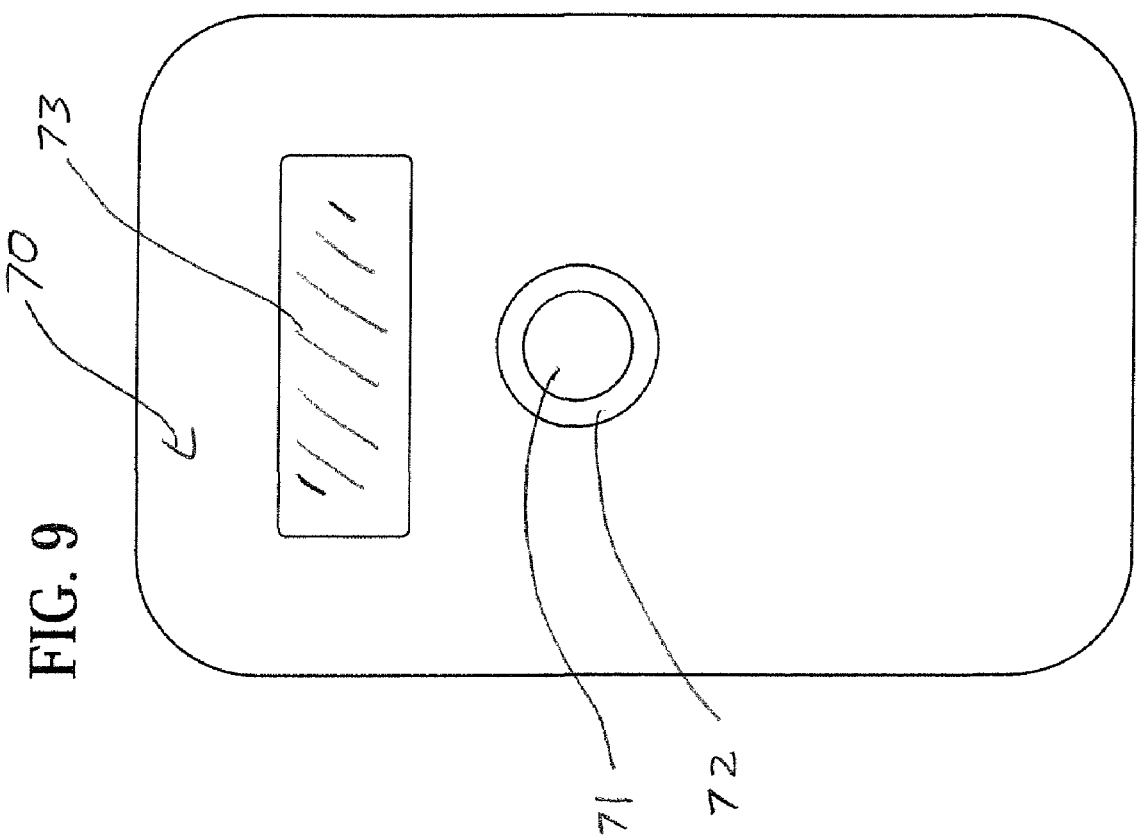
FIG. 9 shows a sheet that is used in the assembly shown in FIG. 1.

An eyepiece 66 of an endoscope 65 (FIG. 1) is locked to the block 40 using the eyepiece-locking plate 50. Initially, the eyepiece-locking plate 50 is positioned in the slot 48 such that the first side section 52 of the central opening 51 in the locking plate generally lines up with the cylindrical cavity 46 in the block. This position of the locking plate relative to the block is shown in FIG. 5. The eyepiece of the endoscope is then positioned in the cavity 46 from the front of the support block such that the end of the eyepiece contacts or nearly contacts the barrel of the digital camera, which penetrates the cavity in the block from the back of the block. The eyepiece is locked into position by sliding the locking plate 50 in the slot 48 so that the second side section of the central opening 53 in the locking plate comes into contact with the eyepiece. Owing to the similarity of the radiuses of the second side section and the eyepiece, most or all of the inner surface of the second side section of the central opening in the locking plate contacts one side of the outer surface of the eyepiece. At the same time, the contact between the second side section and the one side of the outer surface of the eyepiece pushes the eyepiece slightly so that the opposite side of the outer surface comes into close contact with the wall of the cylindrical cavity 46 in the block 40. When the locking plate is slid such that the second section 53 of the opening therein comes into contact with the eyepiece, the hole 55 in the locking plate will align with a threaded hole in the block 40. A screw (not shown) can then be passed through the hole 55 in the locking plate and threaded into the hole in the block 40. The close contact of the eyepiece with the locking plate on one side and the wall of the cavity 46 in the block 40 on the other side will restrain the eyepiece to the block.

A sheet 70 includes an opening 71 (FIG. 9) in a central portion thereof. The opening 71 is shaped and sized to accommodate the eyepiece 66 of the endoscope 65. A gasket 72 surrounds the opening 71. The opening in the sheet can fit over the outer circumference of the eyepiece. Alternatively, the opening 71 can be located at the interface between the eyepiece and the rest of the endoscope. The sheet is sized so that it can drape over the digital camera 60, the camera bar 10, the second bar 20, the bracket 30, and the block 40. The opening 71 in the sheet 70 prevents the sheet from interfering with the transmission of light through the endoscope.

The purpose of the sheet is to maintain the sterility of the environment. The side of the sheet that will be exposed to the outside when the sheet is draped over the camera is kept in a sterile condition. Because of the sheet, the rest of assembly 100 and the camera do not have to be sterile. After the camera is secured to the endoscope, a doctor with sterile hands can drape the sheet over the camera and the assembly by picking up and manipulating the sheet on its sterile side. The sheet contains a window 73 made of non-visually-distorting clear material. The window 73 is located such that buttons on the camera and any LCD screen 62 on the back face of the camera are visible when the sheet is draped over the camera. Alternatively, the entire sheet 70 can be made of a clear material as shown in FIG. 1. An additional utility of the sheet is that it prevents fluid that may be sprayed in the direction of the camera from contaminating the camera. To that effect, the gasket 72 creates a seal between the sheet 70 and the eyepiece 65 at the opening 71.

A method for securing a digital camera 60 to the eyepiece of an endoscope using the embodiment of the invention described above will now be explained. A digital camera is placed on the camera bar 10 such that its bottom surface contacts the top surface of the camera bar. The digital camera is positioned so that its tripod mounting hole lines up with one of the three holes 12 in the camera bar. Preferably, the hole 12 on the camera bar with which the tripod mounting hole is aligned is chosen so that the digital camera is centered on the camera bar as much as possible. A screw 90 is then passed from the bottom of the camera bar through the hole in the camera bar aligned with the tripod mounting hole, and then is threaded into the tripod mounting hole. The power of the camera is then turned on—if it is not already on prior to mounting it to the camera bar—and the barrel of the camera is fully extended.

Next, the block 40 is adjusted in three orthogonal linear dimensions so that the end of the barrel of the camera penetrates the cylindrical cavity 46 in the block from the back side of the block. This is accomplished by adjusting the second bar 20 relative to the camera bar 10 along the first axis 81, adjusting the bracket 30 relative to the second bar 20 along the second axis 82 and adjusting the block 40 relative to the bracket 30 along the third axis 83. When the support block is properly positioned, the first, second and third set screws 23,35,45, which are respectively located on the second bar 20, the bracket 30 and the block 40 are tightened to lock the block 40 into place relative to the camera bar 10.

Next, the eyepiece-locking plate 50 is inserted in the slot 48 in the block 40 and positioned so that the first opening section 52 of the locking plate generally lines up with the cavity 46 in the block. The eyepiece is then inserted inside the cavity so that it contacts or nearly contacts the end of the barrel of the camera and is held in that position. Because the radius of the first opening section 52 is larger than the radius of the eyepiece, the first opening section is not effective to lock the eyepiece to the block 40. The eyepiece-locking plate 50, however, is then moved in the slot 48 so that the second opening section 53 surrounds the eyepiece. When the eyepiece-locking plate 50 is properly positioned, the hole 55 in the locking plate will line up with a threaded hole in the block 40. A screw (not shown) can then be inserted to secure the eyepiece-locking plate to the block, thereby securing the eyepiece to the block. The sheet 70 is then draped over the assembly and the camera. This step can be performed by someone who has sterile hands, such as an operating or examining surgeon.

In the method described above, the sequence of many of the steps can be interchanged. For example, the eyepiece can be secured to the block 40 using the eyepiece-locking plate 50 before the block 40 is adjusted relative to the camera bar 10.

Modifications from what is described above are, of course, contemplated. For example, the eyepiece may be secured to the block 40 by a mechanism other than eyepiece-locking plate 50. A sterile bag can be used instead of sheet 70. Further, in other embodiments of the invention, the dovetail connection between the camera bar and the second bar, between the second bar and the bracket and between the bracket and the block are replaced with another connection that allows relative movement along a single axis. Additionally, devices other than set screws can be used to selectively lock one component relative to another component. For example, the camera bar may have a track and the second bar may include a bolt that can be moved within the track. When the second bar is adjusted relative to the camera bar, the second bar can be fixed relative to the camera bar by tightening a nut on the bolt or by rotating a latch. As another example, a ratchet mechanism can be used between two components to allow one of the components to move relative to the other component and to allow the one component to be selectively locked in place relative to the other component.

While particular embodiments of the present invention(s) have been illustrated and described herein, the present invention(s) should not be limited to such illustrations and descriptions. It should be apparent that additional changes and modifications may be incorporated and embodied as part of the present invention(s) within the scope of the following claims.

What is claimed is:

1. An assembly comprising:
   a camera bar;
   a second bar slidably connected to the camera bar such that the camera bar and the second bar can move relative to each other along a first axis;
   a bracket slidably connected to the second bar such that the bracket and the second bar can move relative to each other along a second axis that is orthogonal to the first axis;
   a block slidably connected to the bracket such that the block and the bracket can move relative to each other along a third axis that is orthogonal to both the first axis and the second axis; and
   wherein:
      the camera bar is adapted to be connected to the bottom of a digital camera; and
      the block includes a cavity that is adapted to receive the barrel of a digital camera and an eyepiece of an endoscope.

2. The assembly of claim 1, further comprising:
   a dovetail connection between the camera bar and the second bar.

3. The assembly of claim 1, further comprising:
   a dovetail connection between the second bar and the bracket.

4. The claim of claim 1, further comprising:
   a dovetail connection between the bracket and the block.

5. The assembly of claim 1, wherein the camera bar has three holes, each one of the three holes is adapted to receive a screw, the screw further being adapted to be received by a tripod mounting hole in a digital camera.

6. The assembly of claim 1, further comprising:
   a set screw for preventing relative movement between the camera bar and the second bar;
   a set screw for preventing relative movement between the second bar and the bracket; and
   a set screw for preventing relative movement between the bracket and the block.

7. The assembly of claim 1, further comprising an eyepiece-locking plate slidably connected to the block.

8. The assembly of claim 7, wherein:
   the eyepiece-locking plate includes an opening having a first side and a second side;
   the first side of the opening has a first radius and a second side of the opening has a second radius; and
   the first radius is larger than the second radius.

9. The assembly of claim 8, wherein the opening in the eyepiece-locking plate includes a transition section located in between the first side of the opening and the second side of the opening.

10. The assembly of claim 8, wherein the first radius is larger than the radius of an eyepiece of an endoscope.

11. The assembly of claim 7, further comprising:
    means for securing the eyepiece-locking plate to the block in a particular position relative to the block.

12. The assembly of claim 1, further comprising:
    a sheet for covering the camera bar, the second bar, the bracket, the block and a digital camera secured to the camera bar;
    wherein at least one side of the sheet is sterilizable.

13. The assembly of claim 11, wherein the sheet is made of a transparent material.

14. The assembly of claim 11, wherein the sheet is attached to an eyepiece of an endoscope.

15. The assembly of claim 11, wherein the sheet is attached to the block.

16. An assembly comprising:
    a camera bar;
    a second bar;
    means for connecting the camera bar and the second bar such that the camera bar and the second bar can move relative to each other along a first axis;
    a bracket;
    means for connecting the second bar and the bracket such that the second bar and the bracket can move relative to each other along a second axis that is orthogonal to the first axis;
    a support block;
    means for connecting the bracket and the support block such that the support block and the bracket can move relative to each other along a third axis that is orthogonal to both the first axis and the second axis; and
    wherein the camera bar is adapted to be connected to the bottom of a digital camera, and the block includes a cavity that is adapted to receive the barrel of a digital camera and an eyepiece of an endoscope.

17. The assembly of claim 16, further comprising:
    means for selectively preventing relative motion between the camera bar and the second bar;
    means for selectively preventing relative motion between the second bar and the bracket;
    means for selectively preventing relative motion between the bracket and the block.

18. The assembly of claim 16, further comprising:
    means for locking an eyepiece of an endoscope to the support block.

19. The assembly of claim 16, further comprising:
    means for covering the camera bar, second bar, bracket, support block, and a digital camera secured to the camera bar.

* * * * *